Figure 2:
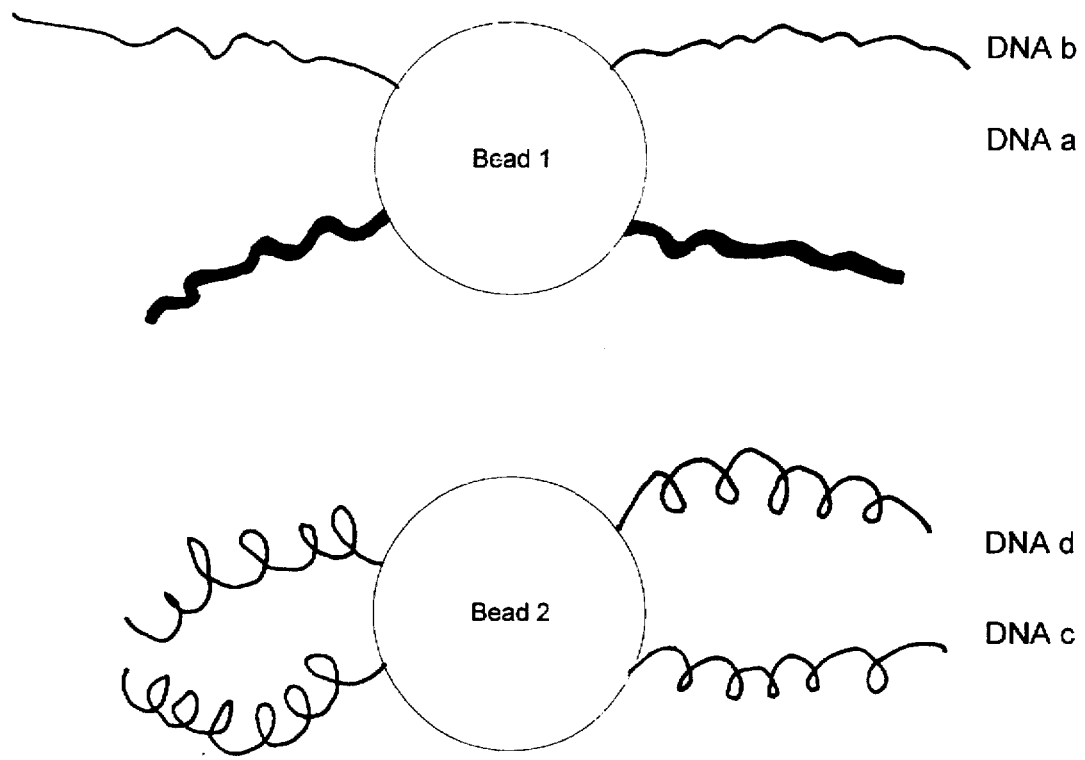

US005763176A

United States Patent [19]
Slater et al.

[11] Patent Number: 5,763,176
[45] Date of Patent: Jun. 9, 1998

[54] METHODS AND DEVICES FOR MARKING A SOLID AND SUBSEQUENTLY DETECTING THE MARKINGS

[76] Inventors: James Howard Slater, 38 Heol-Y-Delyn, Lisvane, Cardiff CF4 5SR; John Edward Minton, 2 Mill Place, Lisvane, Cardiff CF4 5TF, both of Great Britain

[21] Appl. No.: 578,619
[22] PCT Filed: Jul. 12, 1994
[86] PCT No.: PCT/GB94/01506
  § 371 Date: Mar. 29, 1996
  § 102(e) Date: Mar. 29, 1996
[87] PCT Pub. No.: WO95/02702
  PCT Pub. Date: Jan. 26, 1995

[30] Foreign Application Priority Data
Jul. 12, 1993 [GB] United Kingdom ............... 9314394

[51] Int. Cl.$^6$ .................. C12Q 1/68; C07H 21/04; G01P 13/00
[52] U.S. Cl. .................. 435/6; 435/4; 435/912; 536/24.3; 536/24.33; 252/305; 364/550; 364/478.03; 935/78
[58] Field of Search .................. 222/5, 39; 252/305; 435/6, 91.1, 91.2, 4; 364/500, 550, 478.03; 536/24.3, 24.33; 935/77

[56] References Cited

U.S. PATENT DOCUMENTS 3,853,987 12/1974 Dreyer .................. 424/1

FOREIGN PATENT DOCUMENTS

| WO 87/06383 | 10/1987 | WIPO. |
|---|---|---|
| WO 90/06045 | 6/1990 | WIPO. |
| WO 90/14441 | 11/1990 | WIPO. |
| WO 91/17265 | 11/1991 | WIPO. |
| WO 92/01812 | 2/1992 | WIPO. |
| WO 94/04918 | 3/1994 | WIPO. |

OTHER PUBLICATIONS

International Search Report; PCT/GB94/01506; 28 Sep. 1994; Osborne, H.

Primary Examiner—Carla J. Myers
Attorney, Agent, or Firm—Fish & Richardson P.C.

[57] ABSTRACT

A method of marking a solid article or item comprises applying thereto beads having nucleic acids attached thereto. A method of monitoring an interaction between any material, article or item and a person or animal comprises providing a device capable of producing an aerosol containing a nucleic acid label and means to activate the aerosol on interference by a person or animal with the material, article or item. Methods of marking a material comprise adding to the material a plurality of beads having attached thereto a plurality of nucleic acid molecules. At least two distinct primer sequences are associated with different nucleic acid molecules.

12 Claims, 2 Drawing Sheets

Signal from material,
item or article to
release compressed
air propellant to → 3
generate
the aerosol Aerosol

1

Canister of
propellant,
e.g.,
compressed air

2

Container with
microbeads labelled
with attached unique
DNA molecules

Figure 1

METHODS AND DEVICES FOR MARKING A SOLID AND SUBSEQUENTLY DETECTING THE MARKINGS

This invention relates to a security device and a method which enables an ultrasensitive microtrace to be used to demonstrate a direct relationship or interaction between any material, article or item (solid, liquid or gaseous) and man under appropriate conditions where it is required to demonstrate that a relationship or interaction occurred. In particular the security device will demonstrate that a given individual or individuals attempted to steal or did steal a material article or item protected by the security device.

The present invention also relates more generally to methods of marking a material and subsequently detecting that the material has been marked and identifying the marker.

There is a widespread requirement to be able to trace the path taken by a given material as it moves from one location to another. The movement may be of natural materials (e.g. the flow of water in sub-surface aquifers) or materials which have been processed or manufactured by man (e.g. any article constructed by man in a manufacturing process or natural resources such as grains and minerals). In all these situations there may be reasons why it is necessary to develop specific procedures to trace these movements. It may be that direct observation is not possible, e.g., when following the path of a stream underground. It may be that it is necessary to monitor the movement of goods without the direct knowledge of the transporters or, for legal reasons, to prove that the appearance of a material at a particular point in the biosphere was due to at the same material originating from a known starting point.

For example, the articles of manufacture may be stolen in transit or resold at a much lower price than that set by the supplier by an unscrupulous distributor for example car boot sales. A key problem in bringing a conviction is identification of the particular articles sold, to establish that the goods have been stolen or resold from a particular distributor. Problems also occur with liquids such as petroleum which are routinely washed out of carriers into the sea. It is almost impossible to identify which carrier has discharged the oil and as such prosecutions and convictions for polluting the seas are rarely brought.

Further problems are associated with the movement of natural materials, for example the movement of grain. It is particularly difficult to distinguish one batch of such natural materials from another. In the case of grain, problems occur in the European Community with the grain being moved across several different borders to collect a number of EU subsidies for the same batch of grain. A method of marking the grain which may be readily detected is necessary to prevent such fraud.

Our co-pending patent application published under No. WO91/17265 discloses in general terms ways in which materials may be labelled in particular using a DNA molecule to label the material. Our co-pending PCT application published 3 Mar. 1994 under No. WO94/04918, discloses a method of marking a liquid in particular with two labels one of which is not a nucleic acid tag and one of which comprises DNA molecules. In each case, the unique microtrace comprising DNA molecules is added to the material, the resulting material is sampled after movement thereof, and the presence of the microtrace additive in the sample is detected, analyzed and decoded.

In a preferred aspect described, the material being monitored is a liquid hydrocarbon, such as oil, and the microtrace additive is designed such that it cannot be easily removed from the hydrocarbon by aqueous washing. Various methods are proposed for ensuring that the DNA microtrace remains in the hydrocarbon rather than partitioning into the aqueous phase, including linking the DNA to hydrophobic beads typically of from 1 to 5 µm diameter, designed to be retained in hydrocarbons and not the aqueous phase. A method of marking a liquid and subsequently detecting that the liquid has been marked is disclosed, which method comprises: adding to the liquid an additive comprising a plurality of particles in an amount no greater than 1 part by weight of particles per $10^6$ parts by weight of liquid, the particles comprising signal means to aid their detection and not being visible in the liquid to the naked eye; sampling a portion of the liquid containing the said additive; detecting the presence of particles in the sample, with the proviso that the said signal means does not consist solely of a nucleic acid tag.

The previous applications and uses of microtrace DNA labels are primarily concerned with the labelling of liquids and in particular with hydrocarbons. There is no disclosure of how the labelling of manufactured or natural articles, in particular solid articles might be performed.

In a first aspect of the invention there is provided a method of marking a solid article or item comprising applying to said article microbeads having nucleic acids attached thereto.

The previous inventions deal with the type of particles, their size, marker properties, methods of application and detection, as well as aspects of the unique DNA molecules used to provide the unique labels. In all these applications the use of the microtrace DNA labels involves the addition to the material of the label comprising a single DNA sequence for each material, which is subsequently detected after a period of time during which time the material may have been moved. Knowledge of the unique nature of the DNA molecule, in particular a secret but predetermined sequence of bases within the DNA microtrace molecule enables the origin and movement path of the labelled material to be determined with complete accuracy.

A problem with the prior publications is the requirement that each DNA must be essentially distinct from other DNAs to provide the required specificity.

In a second aspect of the invention there is provided a method of marking a material comprising adding thereto a plurality of microbeads having attached thereto a plurality of nucleic acid molecules, at least two distinct primers being associated with different nucleic acid molecules.

The prior art uses of the microtrace DNA labels do not envisage the transfer of the label from the material to any agent, especially man, who may legitimately or illegitimately be involved with the movement of the labelled material, article or item. There is also a need to be able to protect any material, article or item by showing that an individual or individuals have been in contact with the labelled material, article or item. This is particularly important in the case of any material, article or item which is being transported from one place to another and may be a target for theft or damage. The invention will not prevent a theft occurring, except in the general sense of providing an additional deterrent which may cause potential thieves to desist, but will provide means of uniquely and unequivocally linking a thief or potential thief to the labelled material, article or item.

In a further aspect of the present invention, there is provided a method of monitoring an interaction between any material, article or item and a person or animal comprising providing a device adapted to produce an aerosol containing a nucleic acid label and means to activate said aerosol on interference by a person or animal with the article, material or item.

The general principle is to place a device on, within or close to the material, article or item to be protected. The device is capable of generating an aerosol, upon a predetermined signal, to disperse a microtrace DNA label sufficiently widely, rapidly and effectively to be able to-ensure that some of the DNA microtrace label is deposited on the agent, especially on an individual or individuals, which may be attempting to remove (steal) the material, article or item.

The microtrace aerosol may be a canister pressurised with a propellant e.g. an aerosol product or compressed air and containing the DNA microtrace label, placed within a container, such as a suitcase or shipping container, only to be activated if the container is opened in some way by an individual who does not know how to disarm the microtrace aerosol prior to attempting to open the container. The act of opening the container may in some way be used to trigger the microtrace aerosol and disperse the DNA microtrace into the atmosphere with sufficient force that the individual opening the container will inevitably be layered with the microtrace. Subsequently samples from the individual exposed to the aerosol may be taken, for example, from skin or from the fibres of clothes, and the microtrace label analyzed.

The label may be in the form of a bead which has at least one nucleic acid molecule attached thereto and typically has between 100–4000 nucleic acid molecules attached. The beads are typically formed of a polymeric material but may also be formed from natural materials such as silica and generally have a diameter within the range from 0.05 μm to 100 μm, preferably within the range from 0.01 to 5 μm. Exemplary microbeads/spheres are commercially available from Dynal (UK) Ltd of Wirral, Merseyside, United Kingdom under the generic tradenames of DYNABEADS and DYNASPHERES. The preparation of these beads is disclosed in e.g. European Patent Publication Nos. 91453, 10986 and 106873 and U.S. Pat. Nos. 4186120, 4530956, 4563510 and 4654267. The DNA is attached to the bead through biotin-streptavidin or neutralite binding or through direct —COOH or —NH$_2$ mediated or other covalent links.

Additional features of the microtrace aerosol may aid the detection of individuals who have been exposed to the aerosol. For example additional beads having a fluorescent label might be included in the aerosol or the nucleic acid labelled beads may be fluorescently labelled and may be detected in situ, e.g. on skin or clothes, as a visual signal generated when appropriate light is shone on the beads to activate the fluorescent label. Alternatively a dye of some nature may be included in the aerosol, and the first stage of detection will be to define a region of skin or clothing which shows the presence of the dye, providing initial evidence that this may be the region to examine more closely for the presence of the microtrace label in order to find and isolate the DNA microtrace beads. Alternatively beads may be provided with half of a specific binding pair e.g. antigen or antibody, may be radiolabelled, magnetic or include enzymes to said detection.

The device may be modified to provide systems for protecting property as part of a house or business property security system such that in the event of illegal entry the device may be activated to spray intruders with a unique microtrace label which might facilitate the detection and unequivocal identification of the intruder. Another modification of the basic device might be as a car alarm system that sprays intruders who illegally enter a vehicle. In addition to the usage envisaged above where the device is passively activated, for example, when a suitcase is tampered with, the aerosol device may also be used knowingly by one individual who holds the device or is in a position to activate the device. For example, the microtrace aerosol might be used as the basis of a personal protection device to spray unique labels onto an attacker or potential attacker. The basic device may be modified to any circumstances in which the transfer of the microtrace label by an aerosol to identify a second individual or material, article or item might be advantageous.

Retail articles or natural products to be labelled according to the invention may be sprayed using an aerosol device or alternatively the beads may be otherwise applied e.g. by painting on in liquid form or a suspension of beads incorporated in a pen for marking the article. The beads may be incorporated in an ink to be printed on the article or packaging for the article. The beads may be applied to a small region of the article, identifiable by the marker or supplier so that no additional label is required to detect the presence of the beads, but the beads may be directly isolated from the relevant portion of the article for analysis. The method by which the beads are applied will vary depending on the article to be labelled. For example, grain could be sprayed with the beads at an appropriate point in the processing in the same manner that the grain might be sprayed with fungicide whereas a small region of a retail article could be labelled perhaps by applying the beads to a small area of the article using a pen to deposit the bead suspension.

In each case, either the whole stock issuing from a particular manufacturer might be labelled, so that each batch might be specifically tagged. Alternatively, batches being delivered to distributors who were under suspicion might be labelled, or random batches tagged to act as a deterrent to would-be fraudsters.

The beads may be suspended in solution for example an aqueous solution between 10–100,000 beads per ml. Once the solution has dried, the beads adhere to the surface to which they have been applied. Lacquers or adhesives may be incorporated into the solution to aid adhesion. Alternatively a layer of lacquer or adhesive may be applied over the microbeads to protect them from wearing off.

The DNA coated microbeads are reasonably resilient. In the dry form, the DNA is not readily susceptible to the attack of nucleases and so, for example, may successfully be used to label grain. Alternatively, the DNA may be modified to increase resistance to nuclease attack. Given that the labels are often used to monitor retail items during transportation and initial sales, they do not come into contact with extremes of heat which otherwise might damage the DNA. DNA can withstand some UV exposure. While strong UV might cause damage, this would be pinpointed to one portion of the microbead only and DNA present in the remainder of the beads could still usefully be detected and analyzed.

The article, material or item bearing the DNA labelled beads may be analyzed, firstly to detect whether DNA labelled beads are present and where they are located using, for example, the fluorescent or magnetic property of the bead. The beads provide a focal point for the DNA allowing the DNA to be more readily analyzed and detected. Following location of the beads, the beads may be washed out of or off the material or article or clothing of a person and the polymerase chain reaction (PCR) performed directly on the DNA labelled beads using appropriate primers. The PCR may be carried out on DNA which has been detached from the beads although it is preferable and more efficient to carry out the PCR directly on the DNA labelled beads.

The microbeads may be prepared having at least two distinct DNA molecules bound to each bead, the total number of DNA molecules preferably lying within the range of 100–4000 molecules per bead. The distinct DNA molecules have separate primers for PCR, each primer being selected from a different set of primers for example being one of ten known primers. Once a bead has been isolated, the PCR reaction is carried out using each of the primers from the first set and each of the 10 primers from the second set. Successful PCR will indicate which primers are present. This allows for the same pool of DNA primers to be used to generate many easily identifiable DNA molecules and beads which are distinguished from each other.

The invention is hereinafter described in more detail by way of example only with reference to the accompanying drawings in which:

FIG. 1 is a schematic diagram of an aerosol device for dispersing DNA microtrace beads; and FIG. 2 shows four different DNA molecules arranged pairwise on two distinguishable beads.

An apparatus as shown schematically in FIG. 1 designed to produce a suitable aerosol when activated by an appropriate signal from the material, article or item to be protected. The canister contains a suitable propellant (1), e.g. compressed air, which when released generates the aerosol containing the DNA labelled microbeads and any other material from the reservoir (2). The signal may be any electrical signal, mechanical or other physical signal, light signal, magnetic signal, or any other suitable means to open the valve (3) to release the propellant and enable the aerosol to be formed.

The apparatus shown schematically in FIG. 1 is based on a device used for spraying paint by model makers, a Badger Air Brush 100 powered by Humbrol Power pack compressed air. However, other known aerosol devices could be adapted to incorporate the microtrace either for immediate spraying or in a reservoir for later activation or application.

The reservoir (1) contains the microbeads with attached DNA microtrace molecules in suspension. The microtrace beads may be in a gaseous or liquid phase at concentrations which give a high concentration of beads in the aerosol. Typically the beads will be in a concentrated form such that when dispersed in the aerosol, 1 ml of aerosol contains between 10 and $10^8$ beads, although higher and lower bead densities may be suitable for particular applications. Normally the suspending phase will be water but any other liquid will serve as the dispersant for the aerosol.

The microtrace beads may follow any of the formulations previously described. For example, the beads Q-435 from Dyno Particles AS, P.O. Box 160, N-2001, Lillestrom, Oslo, Norway (5.5 μm beads 89.5% polystyrene, 5.5% divinylbenzene and 5% methylmethacrylate coated with streptavidin for attachment of biotin labelled DNA oligonucleotides carrying the known DNA base sequence of the microtrace label) may be used. Further these or other beads labelled with a fluorescent chromaphore, such as Coumarin 6, might be used as an additional indicator of the presence of the microtrace beads from a collected sample. Beads such as Dyno Particles beads MP-887 (0.5 μm diameter with Coumarin 6) or MP-821 (0.25 μm diameter with Coumarin 6) might be used.

The reservoir may also contain separately from the beads additional indicators for the presence of the dispersed aerosol. For example, the gaseous or liquid aerosol might also contain specific dyes, especially fluorescent dyes or other dyes detectable by a range of simple (light) or complex (electron microscopy, flow cytometry, NMR, IR or other spectroscopic techniques) procedures. The purpose of these adjunct components to the microtrace beads will be to provide convenient indicators that the aerosol spray has been deposited on an individual directly, his clothes or other items belonging to the tagged individual. Their purpose will be to indicate quickly and accurately what regions should be sampled in detail to investigate for the presence of the microtrace beads. Because of the lack of variability in the possible number of adjunct dyes or other indicators they will not in themselves give the level of uniqueness possible with the various DNA oligonucleotides used as the key microtrace labels. In addition the aerosol may contain additional material, for example a lacquer such as Humbrol nitrate cellulose dope (Hull UK) or adhesive, to aid the attachment of the microtrace beads to the intended target to ensure that the beads are layered onto and remain on the target individual or material.

The beads are coated (attached either through the binding of biotin—contained within the DNA oligonucleotide—to either streptavidin or neutralite, or bound directly through some kind of —COOH or —NH$_2$ or other mediated covalent chemical link or any other method of securely attaching the DNA molecules stably to the beads) with at least 100 DNA oligonucleotide molecules, typically 2000 molecules, having a known unique label sequence would be suitable.

An aerosol may also be used to spray an article such as grain.

For the grain labelling procedure a mixture of fluorescent, DNA-labelled 0.5 μm diameter beads (MP887 from Dyno) and fluorescent-labelled 4.5 μm diameter beads (FC26 from Dyno) was used. The FC26 beads were selected as suitable beads for rapid identification under UV microscopy. The MP887 beads were used as the DNA carriers. For the two bead mixture in the correct ratios a stock suspension of FC26 beads at $2.7 \times 10^7$ beads ml$^{-1}$ in TE buffer (10 mM Tris-HCl, 1 mM EDTA pH 8.0) was prepared. 100 μl stock FC26 bead suspension was added to 1 ml stock DNA-labelled MP887 suspension. The two bead stock solution was diluted with TE buffer to yield a suspension containing $1 \times 10^6$ FC26 beads ml$^{-1}$ and $1 \times 10^8$ DNA-labelled MP887 beads ml$^{-1}$. 1.0 ml diluted two bead suspension was sprayed onto 100 g wheat grain spread out on a tray and allowed to air dry for a few minutes. Labelled grain was stored in plastic containers at room temperature (ca 15° to 36° C.). Labelling of the grain was shown by epiflourescence microscopy using an excitation wavelength of 495 nm and an emission wavelength of 510 nm, and magnification ranging from x 80 to x 800.

Samples of grain can be routinely analyzed using epifluorescence to check for the presence of fluorescent beads. A wide range of samples have been analyzed following various storage and treatments with 100% success in the case of samples which have been labelled using these procedures. Samples labelled for up to 9 months continue to show the presence of beads with no indication of any significant changes in the number of beads expected to be observed.

5.0 g grain was selected and washed 3 times in 5.0 ml deionised water, and the washings pooled (15.0 ml). The washings were filtered through a series of polycarbonate membrane filters (Nucleopore) in the sequence:

(a) 8.0 μm pore size to remove large particles including any significant grain particles.

(b) 0.8 μm pore size to remove the next size of particles and FC26 beads.

(c) 0.22 μm pore size to remove and concentrate the DNA labelled MP887 beads.

Following each stage the membranes were washed with 5.0 ml deionised water to ensure that all the smaller particles not being retained by the particular filter passed through the membrane. The final 0.22 μm filter was carefully placed in a 1.5 ml plastic tube and 0.1 ml sterile deionised water added. The membrane and water was vortex mixed for 5.0 min to remove the DNA-labelled beads from the membrane. The membrane was removed from the tube and the DNA labelled beads collected as a pellet following centrifugation at 13,000 rpm for 20 min. 900 μl of the bead-free supernatant was carefully removed by pipette without disturbing the bead containing pellet. The beads were then resuspended in the remaining 100 μl sterile water by vigorous vortex mixing. 2.0 μl was checked by epifluorescence microscopy to ensure that the 0.5 μm DNA-labelled MP887 beads had been recovered. The remaining suspension was stored at 0.4° C. for subsequent DNA amplification procedures.

In order to facilitate the construction of large numbers of unique DNA microtrace labels, more than one different DNA oligonucleotide may be attached to the beads. For example, each bead may carry two different DNA molecules (FIG. 2). Moreover, each aerosol or additive may contain more than one recognisably different DNA-labelled bead. The beads might be distinguished on the basis of size, shape, surface architecture, chemical composition, chemical additives (e.g. different metal, dyes, fluorescent dyes, etc) or any other property which would enable a sample to be analyzed for different types of beads.

The two different DNA molecules are recognised by having different primer sequences. A typical construction will be approximately 100 base pairs in length, the first and last 30 base pairs being primers for PCR amplification and the middle region comprising a specific DNA sequence. The specific DNA sequence may either be sequenced from the PCR primers or alternatively from an additional region known as the sequencing primer. An additional sequence may be included between the PCR primer or sequencing primer and specific sequence to ensure that the entire specific DNA sequence may be sequenced.

Where the two DNA molecules are used, either attached to the same or separate beads, different PCR primers are used to distinguish the molecules from each other, the presence of a particular primer being identified by the amplification by PCR of the sequence in the presence of a known primer. Table 7 shows how 3 DNA primers from a 3 dimensional array of primers might be selected for a particular bead.

Referring to table 7 below, two beads are exemplified, each having three DNA molecules having 3 different primers. The first DNA molecule in each case has a primer selected from A–J, the second DNA molecule for each bead has a primer selected from 1–10 and the third DNA molecule on each bead has a primer selected from K to T. In this case the beads have primers C,2,M and E,9,N respectively.

TABLE 7

|    | A | B |   |   |   |   |   |   |   |   |
|----|---|---|---|---|---|---|---|---|---|---|
| P1 | 1– | 1– | C | D | E | F | G | H | I | J |
| P3 P2 | 10 | 10 | 1–10 | 1–10 | 1–10 | 1–10 | 1–10 | 1–10 | 1–10 | 1–10 |
| K |   |   |   |   |   |   |   |   |   |   |
| L |   |   |   |   |   |   |   |   |   |   |
| M |   |   | x |   |   |   |   |   |   |   |
| N |   |   |   |   | x |   |   |   |   |   |
| O |   |   |   |   |   |   |   |   |   |   |
| P |   |   |   |   |   |   |   |   |   |   |
| Q |   |   |   |   |   |   |   |   |   |   |
| R |   |   |   |   |   |   |   |   |   |   |
| S |   |   |   |   |   |   |   |   |   |   |
| T |   |   |   |   |   |   |   |   |   |   |

Once a bead has been isolated, a PCR may be carried out in the presence of each of the primers A–J separately to discover which primer leads to amplification of the DNA indicating the primer present in the first DNA molecule of the bead. Further amplification will identify which of the primers 1 to 10 and K to T are present. If necessary the specific DNA sequence may then be elucidated to fully identify the bead.

The total number of useful unique DNA combinations for a given number of DNA molecules (x) attached to one type of bead is shown in Table 1 and an arrangement matrix in Table 2. Table 3 shows the number of useful unique pairwise bead combinations (p) for a given number of pairwise DNA combinations on each bead (n) and an arrangement matrix in Table 4. For example, for 100 different DNA oligonucleotides and a microtrace product containing two different beads selected from 4 different beads, the total number of unique labels ($73.477 \times 10^6$) is shown in Table 5. A similar table for 200 different DNA molecules and the same number and combination of beads shows that $182.9 \times 10^6$ unique labels may be formed (Table 6). There is no limit to the number of unique microtrace labels since the number of different DNA molecules can be increased or the number of beads in the aerosol or additive increased.

In the case

TABLE 1-continued

Number of useful unique pairwise DNA combinations (n) for a given number of DNA molecules (x) on one bead.

| Total number of DNA molecules available x | Arrangement of useful unique pairwise DNA combinations (see Table 2) | Number of pairwise DNA combinations n | Number of pairwise DNA combinations by formula calculation $n = \{x^2 - x\}/2$ | Number of times one DNA molecule used $\{x - 1\}$ | % use of one DNA molecule $\{x - 1\}*100/n$ |
|---|---|---|---|---|---|
| 100 | bc ... bf<br>cd ... cf<br>de ... df<br>ef<br>etc | etc | $\{10000 - 100\}/2 =$ 4,950 | 99 | 2 |
| 200 | etc | etc | $\{40000 - 200\}/2 =$ 19,900 | 199 | 1 |
| 1000 | etc | etc | 499,500 | 999 | 0.2 |
| $1 \times 10^{18}$ | etc | etc | $5 \times 10^{35}$ | $1 \times 10^{18}$ | $2 \times 10^{-18}$ |

TABLE 2

Arrangement of useful unique pairwise DNA combinations (n) for a given number of DNA molecules (x) on one bead.

|   | aa | ab | ac | ad | ae | af | ag | ah | ai | ax |
|---|---|---|---|---|---|---|---|---|---|---|
| ax | axaa | axab | axac | axad | axae | axaf | axag | axah | axai | axax |
| ai | aiaa | aiab | aiac | aiad | aiae | aiaf | aiag | aiah | aiai | aiax |
| ah | ahaa | ahab | ahac | ahad | ahae | ahaf | ahag | ahah | ahai | ahax |
| ag | agaa | agab | agac | agad | agae | agaf | agag | agah | agai | agax |
| af | afaa | afab | afac | afad | afae | afaf | afag | afah | afai | afax |
| ae | aeaa | aeab | aeac | aead | aeae | aeaf | aeag | aeah | aeai | aeax |
| ad | adaa | adab | adac | adad | adae | adaf | adag | adah | adai | adax |
| ac | acaa | acab | acac | acad | acae | acaf | acag | acah | acai | acax |
| ab | abaa | abab | abac | abad | abae | abaf | abag | abah | abai | abax |
| aa | aaaa | aaab | aaac | aaad | aaae | aaaf | aaag | aaah | aaai | aaax |

B e a d 2 — Bead 1

☐ indicates discarded pairing because only a single DNA molecule on bead

▨ indicates discarded pairing because same pairwise DNA combination elsewhere in the matrix (e.g. ba = ab) - no way of determining DNA order on beads

TABLE 2-continued

Arrangement of useful unique pairwise DNA combinations (n) for a given number of DNA molecules (x) on one bead.

☐ indicates useful unique pairwise DNA combination

See Table 1 for calculations or values of n for different values of x

TABLE 3

Number of useful unique pairwise bead combinations (p) for a given number of pairwise DNA combinations on each bead (n).

| Total number of DNA molecules x | Number of pairwise DNA combinations (see Table 1) n | Number of useful, unique pairwise bead combinations with two DNA molecules per bead by formula calculation (see Table 4) $p = \{n^2 - 2n\}/2$ | Number of times one DNA molecule used in total combinations $\{(x - 1)^2 - (x - 1)\}/2$ | % use of one DNA molecule $\{\{(x - 1)^2 - (x - 1)\}/2\}*100/p$ |
|---|---|---|---|---|
| 100 | 4950 | $\{24,502,500 - 9900\}/2 =$ 12,246,300 | 4851 | 0.04 |
| 200 | 19,900 | $\{396,010,000 - 39800\}/2 =$ 197,985,100 | 19,701 | 0.01 |
| 1000 | 499,500 | $1.247 \times 10^{11}$ | 498,501 | 0.0004 |
| $1 \times 10^{18}$ | $5 \times 10^{35}$ | $1.25 \times 10^{71}$ | $5 \times 10^{35}$ | $4.0 \times 10^{-34}$ |

TABLE 4

Number of useful unique pairwise bead combinations (p) for a given number of pairwise DNA combinations on each bead (n).

|   | aa | ab | ac | ad | ae | af | ag | ah | ai | ax |
|---|----|----|----|----|----|----|----|----|----|----|
| ax | axaa | axab | axac | axad | axae | axaf | axag | axah | axai | axax |
| ai | aiaa | aiab | aiac | aiad | aiae | aiaf | aiag | aiah | aiai | aiax |
| B ah | ahaa | ahab | ahac | ahad | ahae | ahaf | ahag | ahah | ahai | ahax |
| c ag | agaa | agab | agac | agad | agae | agaf | agag | agah | agai | agax |
| a af | afaa | afab | afac | afad | afae | afaf | afag | afah | afai | afax |
| d ae | aeaa | aeab | aeac | aead | aeae | aeaf | aeag | aeah | aeai | aeax |
| 2 ad | adaa | adab | adac | adad | adae | adaf | adag | adah | adai | adax |
| ac | acaa | acab | acac | acad | acae | acaf | acag | acah | acai | acax |
| ab | abaa | abab | abac | abad | abae | abaf | abag | abah | abai | abax |
| aa | aaaa | aaab | aaac | aaad | aaae | aaaf | aaag | aaah | aaai | aaax |

Bead 1

 indicates discarded pairing because same pairwise DNA combination on one of the beads or each pair of bead carries a single DNA molecule

 indicates discarded pairing because same pairwise DNA combination on a pair of beads elsewhere in the matrix (e.g. baaa = aaab) - no way of determining DNA order on beads

 indicates useful unique pairwise DNA combination

See Table 3 for calculations on values of p for different values of n

TABLE 5

Number of useful unique pairwise DNA from 100 different DNA molecules on 2 different beads selected from 4 different beads.

| | n = 4,950 Bead 1 | n = 4950 Bead 2 | n = 4,950 Bead 3 | n = 4,950 Bead 4 |
|---|---|---|---|---|
| Bead 4 n = 4,950 | | | | |
| Bead 3 n = 4,950 | | | | 12.246 × 10⁶ |
| Bead 2 n = 4,950 | | | 12.246 × 10⁶ | 12.246 × 10⁶ |
| Bead 1 n = 4,950 | | 12.246 × 20⁶ | 12,246 × 10⁶ | 12,246 × 10⁶ |

 indicates discarded pairing because same bead used to make pair - cannot be distinguished as different

 indicates discarded pairing because same pairwise DNA combination on a bead pair elsewhere in the matrix - no way of determining DNA order on beads

 each block corresponds to the complete matrix of Table 4

SUMMARY

For 100 different DNA molecules arranged in different pairwise combinations on a mixture of two different beads taken from four different types of bead there are:

$$6 \times 12.246 \times 10^6 =$$

 73.477 × 10⁶ unique labels

TABLE 6

Number of useful unique pairwise combinations of DNA molecules from 200 different DNA molecules on 2 a pairwise lead combination selected from 4 different beads.

| | n = 19,900 Bead 1 | n = 19,900 Bead 2 | n = 19,900 Bead 3 | n = 19,900 Bead 4 |
|---|---|---|---|---|
| Bead 4 n = 19,900 | | | | |
| Bead 3 n = 19,900 | | | | 197 × 10⁶ |
| Bead 2 n = 19,900 | | | 197 × 10⁶ | 197 × 10⁶ |
| Bead 1 n = 19,900 | | 197 × 20⁶ | 197 × 10⁶ | 197 × 10⁶ |

 indicates discarded pairing because same bead used to make pair - cannot be distinguished as different

 indicates discarded pairing because same pairwise DNA combination on a bead pair elsewhere in the matrix - no way of determining DNA order on beads each block corresponds to the complete matrix of Table 4

SUMMARY

For 200 different DNA molecules arranged in different pairwise combinations on a mixture of two different beads taken from four different types of bead there are:

$$6 \times 197 \times 10^6 =$$

We claim:

1. A method of marking a solid and subsequently detecting that the solid has been marked, said method comprising:
   adding to a liquid an additive comprising a plurality of microbeads in an amount no greater than 1 part weight of microbeads per $10^6$ parts weight liquid, said plurality of microbeads comprising two or more signal means to aid their detection and code means to aid identification, said microbeads not being visible in the liquid to the naked eye; said additive comprising either (a) two or more microbeads, each microbead having different signal means, and at least one microbead having a code means or (b) a microbead having two or more different signal means and at least one code means; said code means and one of said signal means comprising a nucleic acid and another of said signal means comprising a non-nucleic acid signal means;
   applying said liquid to said solid and allowing said liquid to dry to mark the solid;
   detecting the presence on the solid of said microbeads having said non-nucleic acid signal means;
   sampling the solid marked with said additive; and
   decoding said code means, thereby detecting that the solid had been marked and identifying the solid.

2. A method as claimed in claim 1 wherein the particles are applied by spraying said solid with liquid containing said microbeads.

3. A method as claimed in claim 1 wherein between $100-10^8$ microbeads are present per ml of liquid.

4. A method according to claim 1 wherein said liquid additionally comprises a lacquer or adhesive.

5. A method according to claim 1 further comprising the step of applying a lacquer or adhesive over said microbeads on said solid.

6. A method according to claim 1 wherein said second signal means comprises a fluorescent dye.

7. A method according to claim 1 in which the solid is selected from the group consisting of an article of manufacture, naturally occurring material, humans and animals.

8. A method as claimed in claim 1, wherein at least two distinct primer sequences are associated with said nucleic acid signal means.

9. A method according to claim 8 wherein said microbeads have an average size from 0.05 to 5 μm.

10. A method according to claim 8 wherein each said microbead has between 100 and 2000 nucleic acid molecules attached thereto.

11. A method according to claim 8 wherein said two distinct primer sequences are attached to the same microbead.

12. A method of monitoring an interaction between any material, article, or item and a person or animal, comprising:

adding to a liquid an additive comprising a plurality of microbeads in an amount no greater than 1 part weight of microbeads per $10^6$ parts weight liquid, said plurality of microbeads comprising two or more signal means to aid their detection and code means to aid identification, said microbeads not being visible in the liquid to the naked eye; said additive comprising either (a) two or more microbeads, each microbead having different signal means, and at least one microbead having a code means or (b) a microbead having two or more different signal means and at least one code means; said code means and one of said signal means comprising a nucleic acid and another of said signal means comprising a non-nucleic acid signal means;

providing a device adapted to produce an aerosol containing the liquid and the additive and means to disperse said aerosol during said interaction; and detecting the presence on said person, animal, material, article, or item of said microbeads having said non-nucleic acid signal means;

detecting the presence on said person, animal, material, article, or item of said microbeads having said signal means comprising a nucleic acid; and decoding said code means, thereby detecting that the person, animal, material, article, or item had been marked by interaction between said material, article, or item and said person or animal.

\* \* \* \* \*